(12) United States Patent
Olesen et al.

(10) Patent No.: US 10,945,700 B2
(45) Date of Patent: Mar. 16, 2021

(54) NON-INVASIVE ESTIMATION OF INTRAVASCULAR PRESSURE CHANGES USING VECTOR VELOCITY ULTRASOUND (US)

(71) Applicant: B-K Medical Aps, Herlev (DK)

(72) Inventors: Jacob Bjerring Olesen, Copenhagen S. (DK); Jorgen Arendt Jensen, Horsholm (DK); Carlos Armando Villagomez-Hoyos, Frederiksberg (DK)

(73) Assignee: B-K Medical Aps, Herlev (DK)

( * ) Notice: Subject to any disclaimer, the term of this patent is extended or adjusted under 35 U.S.C. 154(b) by 581 days.

(21) Appl. No.: 15/555,333

(22) PCT Filed: Jun. 4, 2015

(86) PCT No.: PCT/IB2015/054246
§ 371 (c)(1),
(2) Date: Sep. 1, 2017

(87) PCT Pub. No.: WO2016/139515
PCT Pub. Date: Sep. 9, 2016

(65) Prior Publication Data
US 2018/0035972 A1    Feb. 8, 2018

Related U.S. Application Data

(60) Provisional application No. 62/126,972, filed on Mar. 2, 2015.

(51) Int. Cl.
*A61B 8/04*       (2006.01)
*G01S 15/89*      (2006.01)
(Continued)

(52) U.S. Cl.
CPC .............. *A61B 8/04* (2013.01); *A61B 5/021* (2013.01); *A61B 8/06* (2013.01); *A61B 8/0883* (2013.01);
(Continued)

(58) Field of Classification Search
CPC ......... A61B 8/04; A61B 5/021; A61B 8/0891; A61B 8/0883; A61B 8/06; A61B 8/488; A61B 8/5223; G01F 1/66; G01S 15/8984
(Continued)

(56) References Cited

U.S. PATENT DOCUMENTS 4,678,996 A * 7/1987 Haacke ................. G01N 24/08
                                              324/309
5,477,730 A * 12/1995 Carter ................. G01M 13/045
                                              73/593
(Continued)

FOREIGN PATENT DOCUMENTS

DK   1997000287      1/1998
EP       2769677 A1  8/2014
WO   2003029840 A1  10/2001

OTHER PUBLICATIONS

Mercer ["Acceleration, Velocity and Displacement Spectra—Omega Arithmetic", PROSIG 2007], (Year: 2007).*
(Continued)

*Primary Examiner* — Oommen Jacob
(74) *Attorney, Agent, or Firm* — Anthony M. Del Zoppo, III; Daugherty & Del Zoppo Co., LPA

(57) ABSTRACT

A method for determining pressure gradients with ultrasound data includes acquiring ultrasound data of a vessel and generating a velocity vector profile for flow in the vessel with the ultrasound data. The method further includes computing an acceleration with the velocity vector profile. The acceleration includes at least a temporal acceleration, and
(Continued)

computing the temporal acceleration includes reducing noise from the velocity vector profile and determining the temporal acceleration from the noise-reduced velocity data. The method further includes determining the pressure gradients with the computed acceleration. The method further includes displaying an ultrasound image of the vessel with indicia indicative of the pressure gradients superimposed thereover.

20 Claims, 8 Drawing Sheets

(51) Int. Cl.
| | |
|---|---|
| *A61B 8/06* | (2006.01) |
| *A61B 8/08* | (2006.01) |
| *A61B 5/021* | (2006.01) |
| *G01F 1/66* | (2006.01) |

(52) U.S. Cl.
CPC .............. *A61B 8/0891* (2013.01); *G01F 1/66* (2013.01); *G01S 15/8984* (2013.01); *A61B 8/488* (2013.01); *A61B 8/5223* (2013.01)

(58) Field of Classification Search
USPC .................................................. 600/437, 407
See application file for complete search history.

(56) References Cited

U.S. PATENT DOCUMENTS

| | | | | |
|---|---|---|---|---|
| 5,609,158 | A * | 3/1997 | Chan | A61B 5/0464 600/518 |
| 5,749,364 | A * | 5/1998 | Sliwa, Jr. | A61B 8/08 600/438 |
| 5,946,417 | A * | 8/1999 | Bonneau | G06K 9/00221 375/240.02 |
| 6,002,232 | A * | 12/1999 | McConnell | G05B 5/01 318/611 |
| 6,148,224 | A | 11/2000 | Jensen | |
| 6,725,076 | B1 | 4/2004 | Jensen | |
| 6,859,659 | B1 * | 2/2005 | Jensen | G01S 15/8984 342/108 |
| 8,211,024 | B2 | 7/2012 | Houle et al. | |
| 8,548,778 | B1 * | 10/2013 | Hart | A61B 6/466 703/6 |
| 9,354,447 | B2 * | 5/2016 | Abdollahi | A42B 3/0433 |
| 10,359,515 | B2 * | 7/2019 | Jensen | G01S 15/8915 |
| 2003/0225337 | A1 * | 12/2003 | Scharf | A61B 5/7239 600/508 |
| 2005/0119541 | A1 * | 6/2005 | Lorenz | A61B 5/14532 600/316 |
| 2006/0173319 | A1 * | 8/2006 | Sumi | G01S 7/52042 600/437 |
| 2007/0016037 | A1 * | 1/2007 | Houle | A61B 8/06 600/438 |
| 2007/0016072 | A1 * | 1/2007 | Grunwald | A61B 8/42 600/468 |
| 2013/0226493 | A1 * | 8/2013 | Martinez | G01V 1/364 702/94 |
| 2014/0222354 | A1 * | 8/2014 | Krittian | A61B 5/021 702/54 |
| 2014/0323868 | A1 * | 10/2014 | Ono | A61B 8/463 600/454 |
| 2015/0335308 | A1 * | 11/2015 | Pedrizzetti | A61B 8/5207 600/454 |
| 2016/0361040 | A1 * | 12/2016 | Tanaka | A61B 8/483 |
| 2018/0035972 | A1 * | 2/2018 | Olesen | A61B 8/0883 |

OTHER PUBLICATIONS

Tasu ["Estimation of Pressure Gradients in Pulsatile Flow From Magnetic Resonance Acceleration Measurements", Magnetic Resonance in Medicine 44:66-72 (2000)] (Year: 2000).*
International Search Report for PCT/IB2015/054246 published as WO2016/139515 A1 dated Sep. 9, 2016.
Olesen et al., Non-Invasive Estimation of Pressure Gradients in Pulsatile Flow using Ultrasound, 2014 IEEE International Ultrasonics Symposium, Sep. 3, 2014.
Pedrizzetti, et al., Left Ventricular Fluid Mechanics: The Long Way from Theoretical Models to Clinical Applications, Annals of Biomedical Engineering, Pergamon Press, Oxford, GB., vol. 43, No. 1, Sep. 4, 2014.
Olesen, et al., Noninvasive estimation of 2D pressure gradients in steady flow using Ultrasound, IEEE Trans. on Ultrasonics, vol. 61, No. 8, Aug. 2, 2014.
J. A. Jensen, Estimation of Blood Velocities Using Ultrasound: A Signal Processing Approach, Cambridge University Press, 1996, New York.
Bonnefous et al., A new Velocity Estimator for Color Flow Mapping, In Proc. IEEE Ultrason. Symp., 1986, pp. 855-860.
S. G. Foster, et al., Flow Velocity Profile via Time-Domain Correlation: Error Analysis and Computer Simulation, IEEE_UFFC, 1990, 37, pp. 164-175.
Bonnefous, Measurement of the complete (3D) velocity vector of blood flows, In Proc. IEEE Ultrason. Symp.,, 1988, pp. 795-799.
Jensen, et al., Estimation of blood velocity vectors using transverse ultrasound beam focusing and cross-correlation, In Proc. IEEE Ultrason. Symp., 1999, pp. 1493-1497.
Jensen, et al., A New Method for Estimation of Velocity Vectors, IEEE_UFFC, 1998, 45, pp. 837-851.
Dunmire et al., Cross-beam vector Doppler ultrasound for angle independent velocity measurements, UMB, 2000, 26, pp. 1213-1235.
Jensen et al., Directional Synthetic Aperture Flow Imaging, IEEE_UFFC, 2004, 51, pp. 1107-1118.
L. N. Bohs, et al., Speckle tracking for multi-dimensional flow estimation, UL, 2000, 38, pp. 369-375.
Udesen, et al., High Frame-Rate Blood Vector Velocity Imaging Using Plane Waves: Simulations and Preliminary Experiments, IEEE_UFFC, 2008, 55, 8, pp. 1729-1743.
Jensen, et al., Estimation of velocity vectors in synthetic aperture ultrasound imaging., IEEE_UFFC, 2006, 25, pp. 1637-1644.
Swillens et al., Ultrasound simulation of complex flow velocity fields based on computational fluid dynamics, IEEE_UFFC, 2009, 56, 3, pp. 546-556.
Kripgans, et al., Vector Doppler imaging of a spinning disc ultrasound Doppler phantom, UMB, 2006, 32, pp. 1037-1046.
Yiu, et al., Vector projectile imaging: time-resolved dynamic visualization of complex flow patterns 2014.

* cited by examiner

NON-INVASIVE ESTIMATION OF INTRAVASCULAR PRESSURE CHANGES USING VECTOR VELOCITY ULTRASOUND (US)

RELATED APPLICATION

This application is a national filing of PCT application Serial No. PCT/IB2015/054246, filed Jun. 4, 2015, published as WO2016/139515 on Sep. 9, 2016, and a U.S. Provisional application Ser. No. 62/126,972, filed on Mar. 2, 2015. This application claims priority to PCT application Serial No. PCT/IB2015/054246, published as WO2016/139506 on Sep. 9, 2016, and to U.S. Provisional application Ser. No. 62/126,972, filed on Mar. 2, 2015.

TECHNICAL FIELD

The following generally relates to ultrasound imaging and more particularly to non-invasively estimating intravascular pressure changes with velocity vector ultrasound (US).

BACKGROUND

Abnormal changes in intravascular blood pressure have been an indication of a diseased vessel. The literature indicates that measured pressure variations have been used clinically as a diagnostic marker in assessing the physiological state of a cardiovascular region. Intravascular pressure can be determined by inserting pressure sensing wires or catheters to the femoral artery and threading them to the region of interest. Such a procedure is invasive and has required the use of ionizing radiation for guidance of the pressure sensory device. Unfortunately, invasive procedures leave the patient susceptible to infection, bleeding, etc., and ionizing radiation can damage or kill cells. Furthermore, the literature has indicated that the accuracy of using catheters is greatly dependent on the physical size and shape of the catheter.

A less invasive approach estimates local pressure changes using microbubbles. This approach relies on injecting gas-filled bubbles into the circulatory system to measure the frequency shift that occurred in the scattered spectrum as ultrasonic waves were applied. Unfortunately, this approach requires the injection of microbubbles. A non-invasive approach is based on Doppler ultrasound. This approach includes analyzing audio signals of the frequency shifts received from the mitral jet, which reveals the peak systolic velocity. From this, local pressure gradients are calculated using an orifice equation. This approach is reliant on a single velocity estimate. Unfortunately, this renders the approach sensitive to hemodynamic factors unrelated to the constricted vessel's effect on the peak velocity, e.g. abnormal cardiac output. This approach has been considered in the literature as unreliable.

In view of at least the above, there is an unresolved need for another approach for measuring intravascular blood pressure.

SUMMARY

Aspects of the application address the above matters, and others.

In one aspect, a method for determining pressure gradients with ultrasound data includes acquiring ultrasound data of a vessel and generating a velocity vector profile for flow in the vessel with the ultrasound data. The method further includes computing an acceleration with the velocity vector profile. The acceleration includes at least a temporal acceleration, and computing the temporal acceleration includes reducing noise from the velocity vector profile and determining the temporal acceleration from the noise-reduced velocity data. The method further includes determining the pressure gradients with the computed acceleration. The method further includes displaying an ultrasound image of the vessel with indicia indicative of the pressure gradients superimposed thereover.

In another aspect, an apparatus includes a velocity estimator that processes ultrasound image data acquired by an ultrasound imaging system and generates velocity vector fields based thereon. The apparatus further includes a temporal acceleration processor that processes the velocity vector fields and generates a temporal acceleration, wherein the temporal acceleration processor filters the velocity vector fields while determining the temporal acceleration. The apparatus further includes a spatial acceleration processor that processes the velocity vector fields and generates a spatial acceleration. The apparatus further includes a pressure change estimator that estimates pressure gradients for the ultrasound data based on a model and the temporal and spatial accelerations. The apparatus further includes a display configured to display ultrasound image data and the pressure gradients estimates.

In another aspect a non-transitory computer readable storage medium is encoded with computer executable instructions which when executed by a processor of the computer causes the processor to: determine a spatial acceleration based on velocity vector fields, transform the velocity vector fields to the frequency domain, producing a sum of sinusoids, differentiate a sub-set of the sinusoids satisfying at least one of a predetermined energy of interest or a predetermine frequency range of interest, producing a sum of cosines, reconstruct the sum of cosines to determine a temporal acceleration, and determine a pressure change with the Navier-Stokes equation based on the spatial acceleration and the temporal acceleration.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

The following generally describes a non-invasive approach for estimating intravascular pressure changes from ultrasound imaging data. In one instance, the approach estimates pressure gradients from 2-D or 3-D vector velocity fields. Changes in pressure are then derived using a model based on, e.g., the Navier-Stokes and/or other equations.

Figure 1:
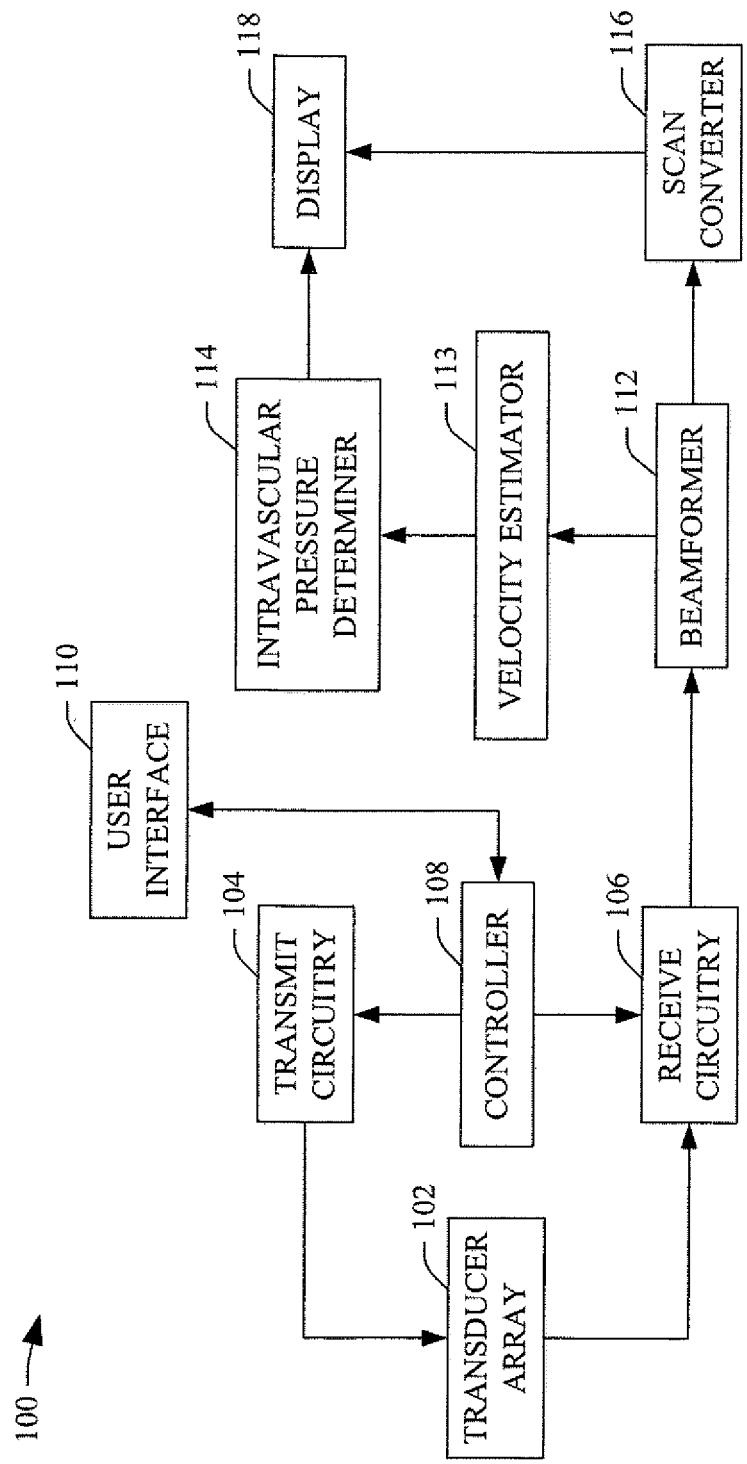
FIG. 1 schematically illustrates an example ultrasound imaging system with an intravascular pressure determiner.

Initially referring to FIG. 1, an example ultrasound imaging system 100 is illustrated.

A transducer array 102 includes a plurality of transducer elements, which are configured to transmit ultrasound signals and receive echo signals. Examples of suitable one-dimensional (1-D) arrays include arrays with 8, 16, 32, 64, 96, 128, 512, etc. transducer elements. Other numbers of elements and/or dimensions (e.g., two-dimensional, or 2-D) are also contemplated herein. The array 102 can be linear, curved, and/or otherwise shaped. The transducer array 102 can be fully populated or sparse and/or a combination thereof.

Transmit circuitry 104 generates a set of pulses that are conveyed to the transducer array 102. The set of pulses actuates a corresponding set of the transducer elements of the transducer array 102, causing the elements to transmit ultrasound signals into an examination or scan field of view. Receive circuitry 106 receives echoes generated in response to the transmitted ultrasound signals from the transducer 102. The echoes, generally, are a result of the interaction between the emitted ultrasound signals and the structure (e.g., flowing blood cells, organ cells, etc.) in the scan field of view.

A controller 108 controls the transmit circuitry 104 and/or receive circuitry 106. In one instance, the controller 108 controls the transmit circuitry 104 to emit waves (e.g., unfocused spherical, weakly focused, plane, etc.) from the aperture by placing virtual sources behind the transducer. A beamformer 112 processes the echoes and generates data at least for generating images and estimating velocity. In one non-limiting instance, this includes generating a sequence of focused, coherent echo samples along focused scanlines of a scanplane.

A velocity estimator 113 is configured to estimate 2-D and/or three-dimensional (3-D) vector velocity fields. For example, the velocity estimator 113 can be configured to estimate a 2-D in-plane vector velocity field $\vec{v}(\vec{r},t)$, $(v_x(t), v_z(t))$. The out-of-plane velocity $v_y(t)$ can be set to zero. Alternatively, the out-of-plane velocity $v_y(t)$ is also determined to estimate a 3-D vector velocity field.

Examples of velocity estimators are described in Jensen et al., "Directional synthetic aperture flow imaging," IEEE Trans. Ultrason., Ferroelec., Freq. Contr., 51:1107-1118, 2004, Jensen et al., "Estimation of velocity vectors in synthetic aperture ultrasound imaging," IEEE Trans. Ultrason., Ferroelec., Freq. Contr., 25:1637-1644, 2006, and Jensen, "Vector velocity estimation using directional beam forming and cross-correlation," U.S. Pat. No. 6,725,076 B1, the entirety of which is incorporated herein by reference.

Other suitable velocity estimators can be based on Jensen, "A New Estimator for Vector Velocity Estimation," *IEEE Trans. Ultrason., Ferroelec., Freq. Contr.*, 48(4):886-894, 2001, and Jensen, "Estimator for Vector Velocity," U.S. Pat. No. 6,859,659 B1, the entirety of which is incorporated herein by reference, and Jensen, "Apparatus and method for determining movements and velocities of moving objects," U.S. Pat. No. 6,148,224, the entirety of which is incorporated herein by reference.

An intravascular pressure estimator 114 is configured to process the velocity vector to estimate a change in intravascular pressure. As described in greater detail below, in one instance this includes smoothing the velocity vector profile, computing a temporal acceleration term from the smoothed velocity vector data, and determining a pressure gradient based on the temporal acceleration term, a spatial acceleration term, and the Navier-Stokes equation. The smoothing, in one instance, de-noises the velocity vector profile. Optionally, the intravascular pressure estimator 114 is further configured to determine pressure drops.

A scan converter 116 scan converts the scanlines for frames of data to generate data for display, for example, by converting the data to the coordinate system of the display. The scan converter 116 can employ analog and/or digital scan converting techniques. A display 118 is configured to display an ultrasound image, an intravascular pressure, a change in intravascular pressure, a pressure drop, etc. The pressure can be visually displayed with indicia (e.g., alphanumeric, graphical, etc.).

A user interface (UI) 110, which includes an input device (e.g., a button, a slider, a touch surface, etc.) and/or an output device (e.g., a visual and/or audible, etc.), provides an interface between the system 100 and a user of the system 100.

It is to be appreciated that the beamformer 112, the velocity estimator 113, the intravascular pressure estimator 114, and/or other components of the system 100 can be implemented via a processor (e.g., a microprocessor, central processing unit, a controller, etc.) executing one or more computer readable instructions encoded or embedded on a non-transitory computer readable storage medium such as physical memory. The processor can additionally or alternatively execute a computer readable instruction carried by a carrier wave, a signal, or other transitory medium.

Figure 2:
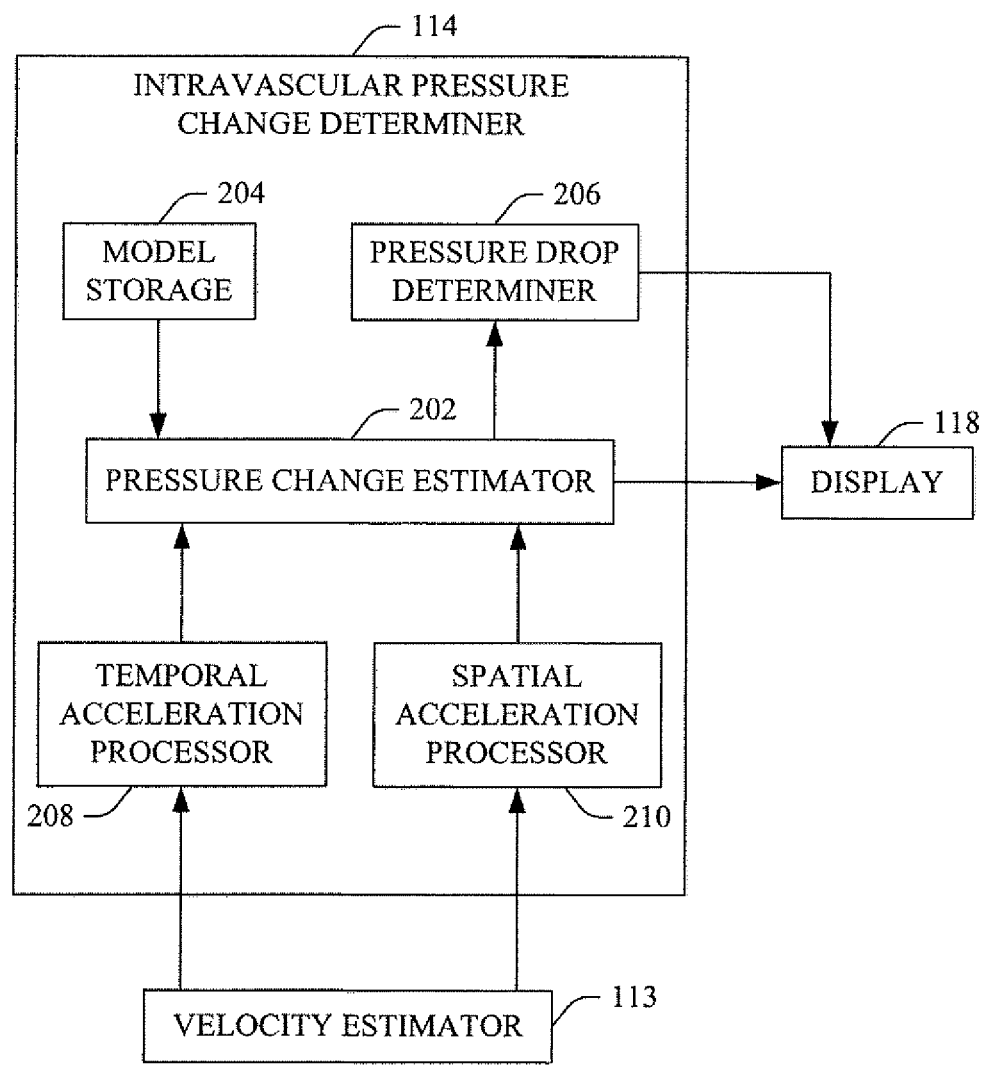
FIG. 2 schematically illustrates an example of the intravascular pressure determiner.

FIG. 2 illustrates an example of the intravascular pressure estimator 114.

The illustrated intravascular pressure estimator 114 includes a temporal acceleration processor 208. In this example, the temporal acceleration processor 208 approximates a temporal acceleration analytically by decomposing a measured flow profile into a series of sinusoids through a Fourier transform. These sinusoids oscillate at frequencies, such as those descriptive for the original profile. The temporal acceleration processor 208 identifies a sub-set of the sinusoids as sinusoids of interest. In one instance, the sub-set includes sinusoids that satisfy energy criterion of interest, e.g., a predetermined number of sinusoids with a highest energy, sinusoids with energy in a predetermined range, etc. In another instance, the sub-set includes sinusoids corresponding to a frequency below a cut-off frequency (e.g., 500 Hz, 1 kHz, etc.). In yet another instance, the sub-set is determined based on a combination of energy and frequency. Other criterion is also contemplated herein.

The temporal acceleration processor 208 differentiates the selected sinusoids. In this example, the temporal acceleration processor 208 computes a first order derivative as shown in Equation 1:

$$\frac{d\vec{v}_m(i, j, t)}{dt} = \sum_{p=1}^{N} |\vec{v}_p(i, j)| 2\pi f_r(i, j) \sin(2\pi f_r(i, j)t - \vec{\varphi}_p(i, j)), \quad \text{Equation 1}$$

where N represents a number of sinusoids used in reconstructing the flow profile, $V_p$ and $\varphi_p$ represents an amplitude and a phase of the frequency component $f_p$, (i, j) represents a position within the each velocity field, and m a direction (e.g., either axial z or lateral x). Taking the derivative computes the temporal acceleration as a sum of cosines. The temporal acceleration processor 208 reconstructs the sum of cosines, e.g., using a trigonometric function, to transform the data back into the time domain. Reconstructing the flow profile as such in connection with cardiac data is possible as the flow is periodic over the cardiac cycle.

With this approach, the velocity profile at each position within the vector field is first transformed from the time domain to the frequency domain, e.g., through a Fourier transform to decompose the vector fields into the frequencies that make it up over a plurality of energy bins. A sub-set of the frequency components is then retained while others are discarded, ignored, etc. In one instance 4 to 12 frequency components, such as 6, 7, 8, 9, 10, etc. frequency components are retained. As discussed above, the selection can be based on energy, frequency, etc. such that a sub-set of the frequency bins are selected. An example where 8 frequency components or bins are selected is discussed below in connection with FIG. 4 herein. The derivative shifts the phase of the selected frequencies by 90 degrees to produce the temporal acceleration profile. This process has the effect of smoothing the original vector velocity estimates, e.g., by removing higher frequency components, which results in higher precision of pressure gradient estimates. The differentiated data is then transformed back to the time domain and further processed as described herein.

The illustrated intravascular pressure estimator 114 further includes a spatial acceleration processor 210. In this example, the spatial acceleration processor 210 calculates a spatial acceleration using polynomial filtering of the measured velocity field. In one instance, the spatial acceleration processor 210 fits a second-order polynomial to a subset of adjacent data points by a linear least-squared approach and then calculates convolution coefficients from a least-squared model, which are used for finding the first-order derivatives. The spatial acceleration processor 210 calculates the axial and lateral derivatives discretely for each position in a scan plane at a given time t.

In one instance, the spatial acceleration processor 210 calculates the axial and lateral derivatives through Equations 2 and 3:

$$\frac{d\vec{v}_m(i,j,t)}{di} \approx \frac{1}{\Delta m} \sum_{p=i-h_w}^{i+h_w} \vec{v}_m(p,j,t)\vec{B}(p-(i-h_w)+1), \quad \text{Equation 2}$$

and $$\frac{d\vec{v}_m(i,j,t)}{dj} \approx \frac{1}{\Delta m} \sum_{p=j-h_w}^{j+h_w} \vec{v}_m^T(p,i,t)\vec{B}(p-(j-h_w)+1), \quad \text{Equation 3}$$

where $\Delta m$ represents a sampling interval of the velocity field in either the axial or lateral direction, p represents an index, $\vec{B}$ represents convolution coefficients, and $\vec{v}_m^T$ represents the transpose of $\vec{v}_m$. The index number p can be found from half a window size of the selected subset, which can be calculated by:

$$h_w = \frac{N_{set}+1}{2} - 1,$$

where $N_{set}$ represents a number of samples in the subset. The convolution coefficients in $\vec{B}$ depend solely on the order of the fitted polynomial and the size of the selected window, which can be found in look-up tables. The multiplication of $\vec{v}_m$ and $\vec{B}$, in this example, is performed element by element.

The illustrated intravascular pressure estimator 114 further includes a pressure change estimator 202. The pressure change estimator 202 is configured to estimate at least an intravascular pressure with the 2-D or 3-D vector velocity fields based on a model. Model storage 204 stores such a model. In the following example, the model is used to determine, from the 2-D vector velocity, in-plane pressure gradients, using the temporal and spatial acceleration (i.e., the temporal and spatial derivatives), as shown in Equations 4A or 4B:

$$\begin{bmatrix}\frac{\partial p}{\partial x}\\ \frac{\partial p}{\partial z}\end{bmatrix} = -\rho \begin{bmatrix}\frac{\partial v_x}{\partial t}+v_x\frac{\partial v_x}{\partial x}+v_z\frac{\partial v_x}{\partial z}\\ \frac{\partial v_z}{\partial t}+v_x\frac{\partial v_z}{\partial x}+v_z\frac{\partial v_z}{\partial z}\end{bmatrix}, \text{ and} \quad \text{Equation 4A}$$

$$\begin{bmatrix}\frac{\partial p}{\partial x}\\ \frac{\partial p}{\partial z}\end{bmatrix} = -\rho\begin{bmatrix}\frac{\partial v_x}{\partial t}+v_x\frac{\partial v_x}{\partial x}+v_z\frac{\partial v_x}{\partial z}\\ \frac{\partial v_z}{\partial t}+v_x\frac{\partial v_z}{\partial x}+v_z\frac{\partial v_z}{\partial z}\end{bmatrix} + \mu\begin{bmatrix}\frac{\partial^2 v_x}{\partial x^2}+\frac{\partial^2 v_x}{\partial z^2}\\ \frac{\partial^2 v_z}{\partial x^2}+\frac{\partial^2 v_z}{\partial z^2}\end{bmatrix} + \begin{bmatrix}\rho g_x\\ \rho g_z\end{bmatrix} \quad \text{Equation 4B}$$

where p represents the pressure, x represents the axial direction, z represents the lateral direction, t represents time, $v_x$ represents the axial velocity component, $v_z$ represents the lateral velocity component, $\rho$ and $\mu$ represents density and viscosity, respectively, and g represents the gravitational force. In general, Equation 4B additionally includes viscous forces and the gravity terms. For Equations 4A and 4B, the out-of-plane velocity $v_y$ and changes in this direction are zero. In a variation, the out-of-plane velocity $v_y$ can be included in Equations 4A or 4B and/or otherwise considered in the determination of the pressure gradients.

Such a model can be based on the Navier-Stokes equation, which is shown in Equation 5:

$$\rho\left[\frac{\partial \vec{v}}{\partial t} + \vec{v}\cdot\nabla\vec{v}\right] = -\nabla p + \rho\vec{g} + \mu\nabla^2\vec{v}, \quad \text{Equation 5}$$

where $\rho$ represents a density of the fluid, $\vec{v}$ represents a velocity vector, $$\frac{\partial \vec{v}}{\partial t}$$

represents a partial derivative of the velocity vector as a function of time, $\nabla$ represents a spatial differential operator $$\left(\frac{\partial}{\partial x}, \frac{\partial}{\partial y}, \frac{\partial}{\partial z}\right),$$

$\vec{v} \cdot \nabla \vec{v}$ represents convective fluid acceleration, $\nabla p$ represents a pressure gradient, $\vec{g}$ represents a gravitational force, $\nabla^2 \vec{v}$ a Laplacian of the velocity field, and $\mu \nabla^2 \vec{v}$ represents a viscous drag caused by the viscosity of the fluid.

Equation 5 describes the development of a fluid's velocity field ($\vec{v}(\vec{r}, t) = v_x(t), v_y(t), v_z(t)$) by relating forces acting on an incompressible volume to acceleration and density at a position $\vec{r}$ and a time t. From Equation 5, the pressure gradient $\nabla p$ can be determined if the three spatial vector components of $\vec{v}$ are known. The gravitational term, in one instance, can be ignored, for example, as a patient undergoing a scan (e.g., ultrasound) is placed in a supine position. The viscous forces, in one instance, can be ignored, for example, when studying blood flow in larger arteries, for example, due to the forces small effect on the overall movement of flow.

Figure 6:
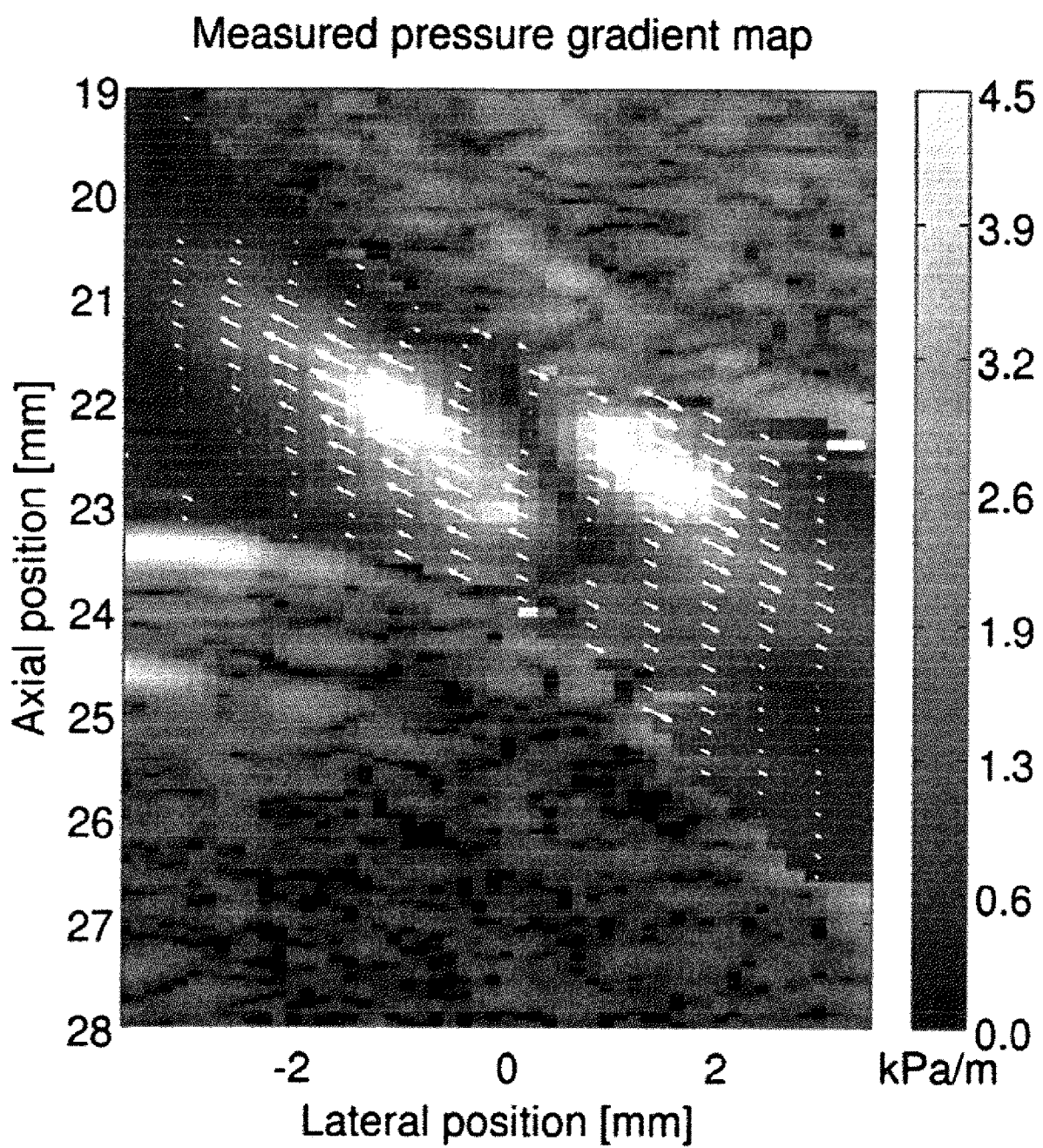
FIG. 6 show results of mapping pressure gradients derived from the velocity data.

A pressure drop determiner 206 determines one or more pressure drops based on the pressure gradients. In another embodiment, the pressure drop determiner 206 is omitted. FIG. 6 below shows an image with pressure gradients (represented via the arrows) superimposed over a vessel in an image. In one instance, a user can identify (via a mouse, etc.) points of interest in the vessel, e.g., behind, within, and before the constriction. The pressure drop determiner 206 determines a pressure drop based on these three points. In another example using FIG. 6, a user can draw a line along the long axis of the vessel running through the constriction. A pressure drop can be determined for a particular moment in time by integrating the pressure gradients along the line in the image. This can be repeated for multiple time points based on each corresponding image. In yet another example, pressure drops can be calculated for a plurality of such lines each time point.

Figure 10:
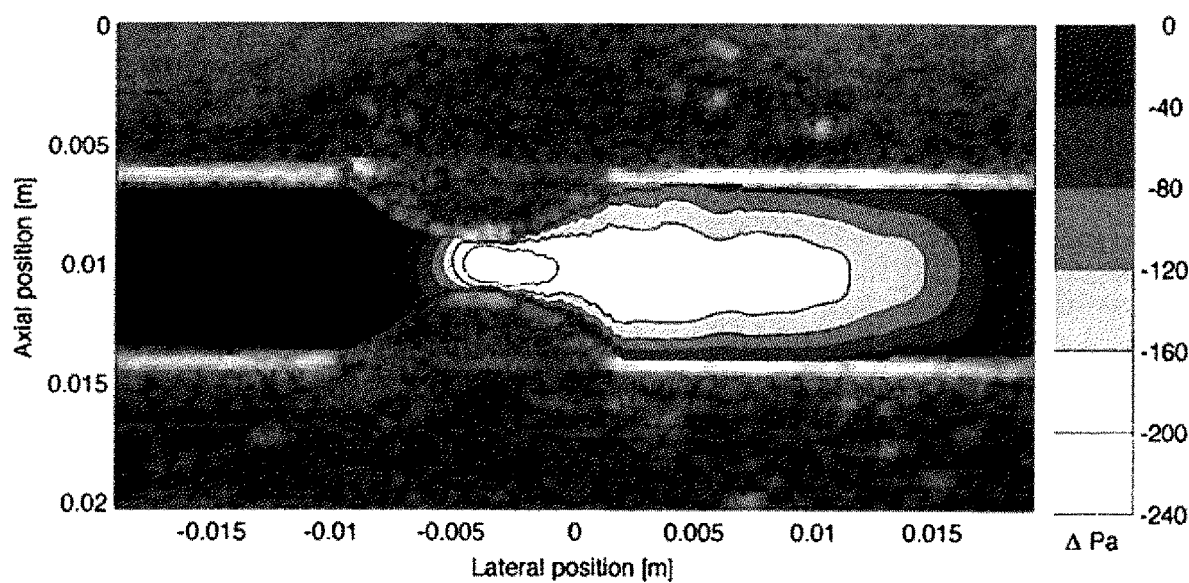
FIG. 10 shows an example display of 2-D pressure changes through a vessel.

The one or more pressure drops can be graphically and/or alpha-numerically presented or displayed via the display 118. For example, the three points and the pressure drop can be superimposed over the image. In another example, the pressure drops for the line can be shown as a plot as a function of time as shown below in FIG. 7. In another example, the pressure drops for the plurality of lines can be shown as a pressure map, e.g., similar to weather map. FIG. 10 shows an example display of 2-D pressure changes through a vessel. The pressure values are given in reference to the entrance of the vessel (left side), which is set to zero. In this case, pressure is derived using EQUATION 6A on multiple streamlines following the vector velocity field.

Figure 3:
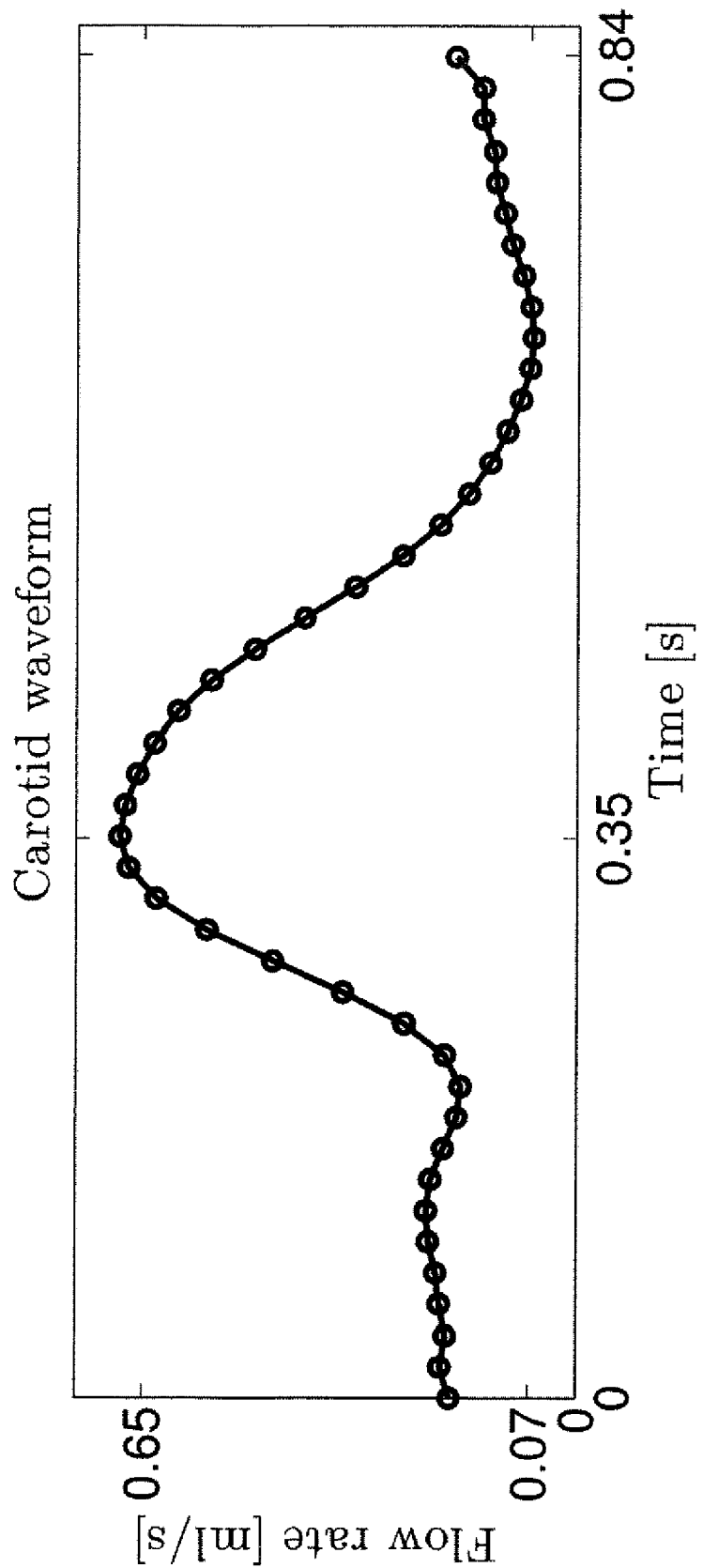
FIG. 3 shows an example inlet profile.

The following describes a non-limiting example that compares an accuracy of the pressure changes using the approach described herein with a simulation. The simulation includes a finite element (FE) model. The geometry of the model is built from segmented MRI data of the flow phantom obtained using a 3-T scanner. The flow parameters of the simulation model are set to mimic actual flow conditions in the experimental set-up. FIG. 3 shows an example inlet profile equivalent to a one measured during experimental settings, which is applied to the entrance of the model. The viscosity (e.g., 4.1 e$^{-3}$ pascal-second, or Pa·s) and density (1,030 kilogram per cubic meter, or kg/m$^3$ are assigned values that match the properties of the blood-mimicking fluid. An example of such a model is discussed in Olesen et al., "Noninvasive estimation of 2-D pressure gradients in steady flow using ultrasound," *IEEE Transactions on Ultrasonics, Ferroelectrics and Frequency Control*, vol. 61, no. 8, pp. 1409-1418.

The experimental set-up and equipment are described next. Vector velocity data are acquired on a flow phantom mimicking the carotid bifurcation having a 70% constriction of the internal branch. Measurements are acquired using a linear array transducer such as the BK8670, a product of BK Medical, DK. The linear array transducer is connected to an experimental research scanner. A three-cycle pulse with a center frequency of 7 MHz is emitted at 12 kHz to a depth of 3 cm. Eight low-resolution images are summed for each high resolution image producing an effective frame-rate of 1,500 Hz. The ultrasound data can be processed on or off-line. The carotid phantom is connected to a flow system capable of generating customized flow waveforms.

Figure 4:
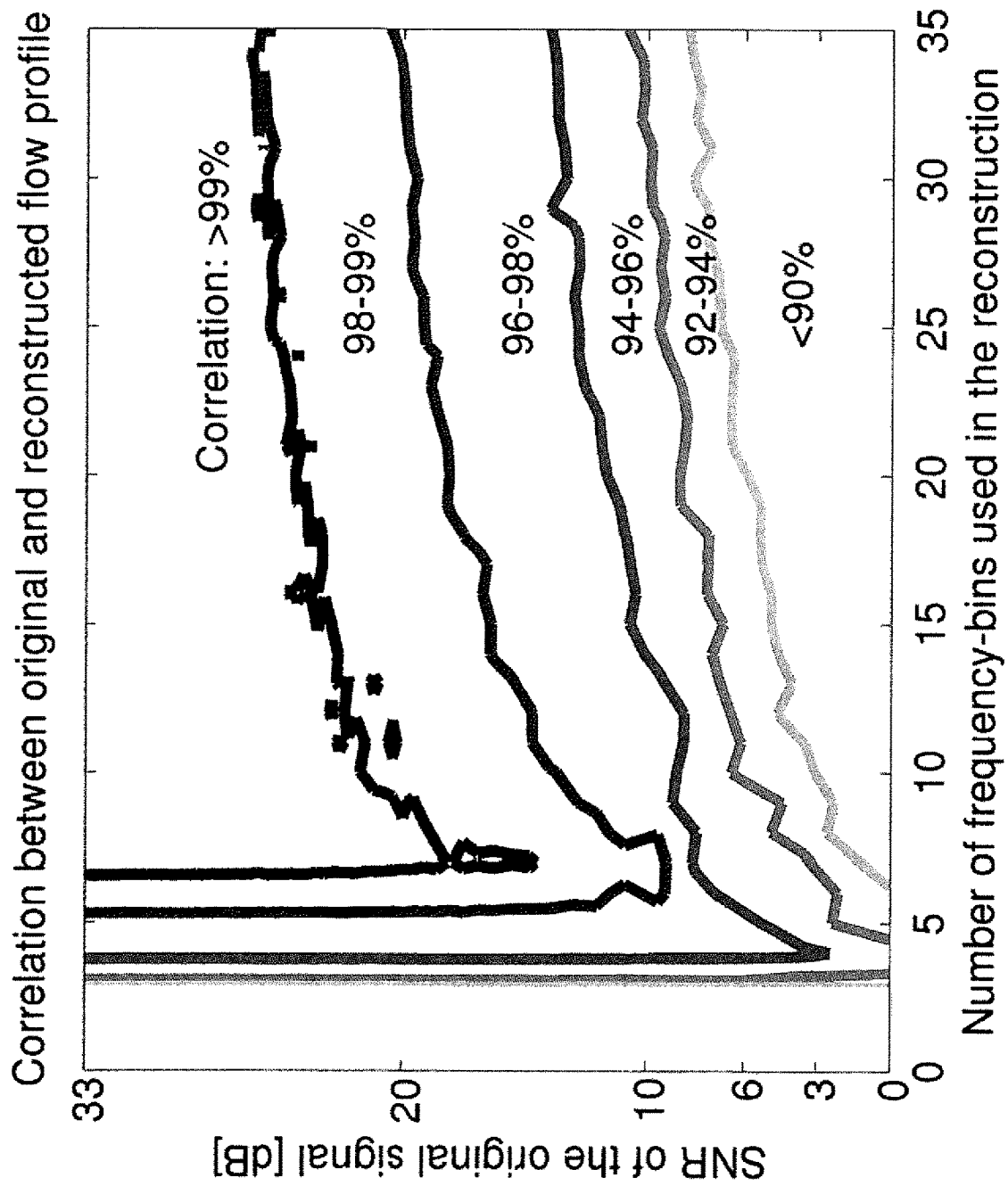
FIG. 4 shows an ideal number of sinusoids needed to reconstruct the profile in FIG. 3.
Figure 5:
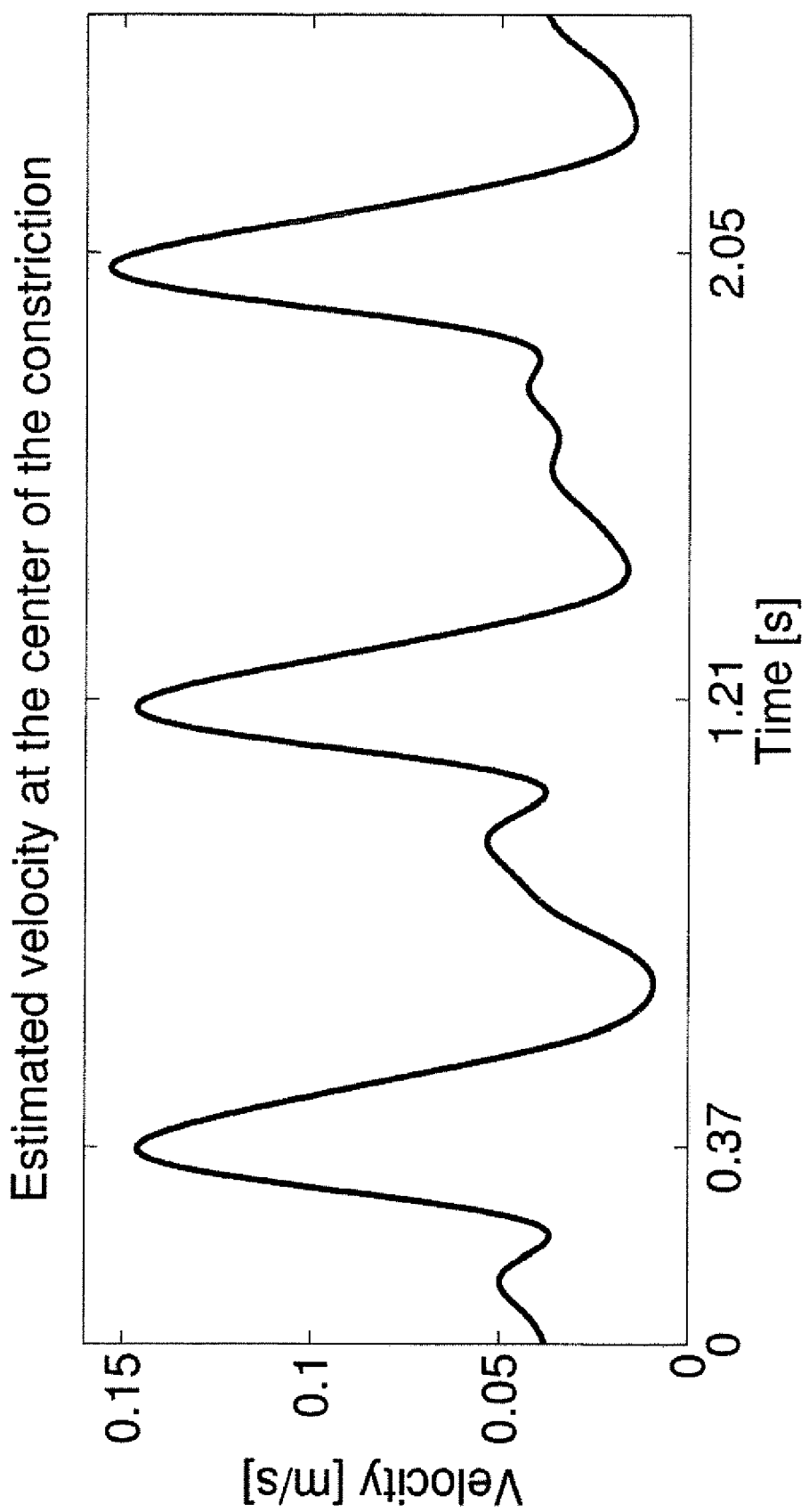
FIG. 5 shows the approximated flow from the center of the constriction.

The local acceleration is approximated by decomposing the measured waveform into a number of sinusoids each oscillating at different frequencies. This is done to express the derivatives for calculating the pressure gradients analytically. The number of sinusoids needed to make a realistic reconstruction of the original flow waveform depends on the complexity of the profile and the amount of noise present in the signal. FIG. 4 shows an ideal number of sinusoids needed to reconstruct the profile in FIG. 3 as a function of an increasing noise level in the measured signal. The system's inlet waveform can be more than 98% recovered from the sum of eight sinusoids, despite having a 20 dB level of white Gaussian noise. The approximated flow from the center of the constriction is plotted in FIG. 5.

Maps of pressure gradients are derived from the velocity data, and a result is shown in FIG. 6. The estimated gradients are plotted during the peak systolic phase of the cardiac cycle. FIG. 6 is calculated using the estimator described in Equation 4A. The arrows and their background gray levels indicate a direction and a magnitude of the gradients, respectively. FIG. 6 shows arrows that tend to point away from the center of the constriction, indicating that a low pressure is present here. The spatial derivatives used in FIG. 6 are calculated using window sizes of 31 (3 mm) and 11 (2 mm) data points for the axial and lateral direction, respectively.

One way of displaying a pressure drop across a region is by using a streamline representation. For instance, adding vector components, $v_x$ and $v_z$, which underlie the streamline, yields the velocity component tangent to the streamline, $v_s$. Re-writing the 2-D in-plane velocity components to a single component parallel to the streamline, means that pressure gradients along the line, can be derived using a 1-D representation of Equation 5, as shown in Equations 6A or 6B:

$$\frac{\partial p}{\partial s} = -\rho \left[ \frac{\partial v_s}{\partial t} + v_s \frac{\partial v_s}{\partial s} \right], \text{ and} \qquad \text{Equation 6A}$$

$$\frac{\partial p}{\partial s} = -\rho \left[ \frac{\partial v_s}{\partial t} + v_s \frac{\partial v_s}{\partial s} \right] + \mu \left[ \frac{\partial^2 v_{xs}}{\partial s^2} \right] \qquad \text{Equation 6B}$$

In general, Equation 6B additionally includes viscous forces and the gravity terms.

The total pressure drop that exists across the streamline is estimated as a function of time. The spatial derivatives, which go into the estimator, are calculated using polynomial filtering. A second-order polynomial is fitted to a subset of 71 adjacent velocity estimates covering a 1.4 mm line of the 10.7 mm long streamline. The window size and the order of the filter is selected to minimize the effect of estimator noise and under the assumption that flow within a 1.4 mm region can be approximated by a second-order polynomial. Each individual gradient gives an indication of how pressure at that particular position changes relative to neighboring pressure values. Summing the discrete contributions from each estimate along the line, the relative drop in pressure that exists between the two ends of the streamline is obtained.

Figure 7:
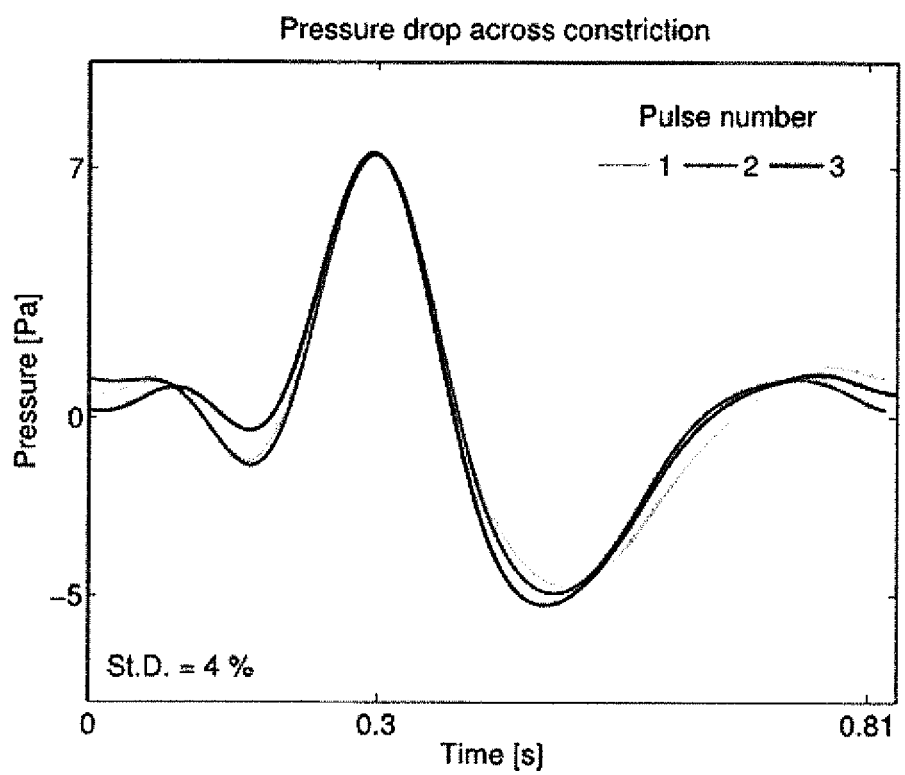
FIG. 7 shows a plot of the temporal evolution of the pressure drop for the three measured cardiac cycles.
Figure 8:
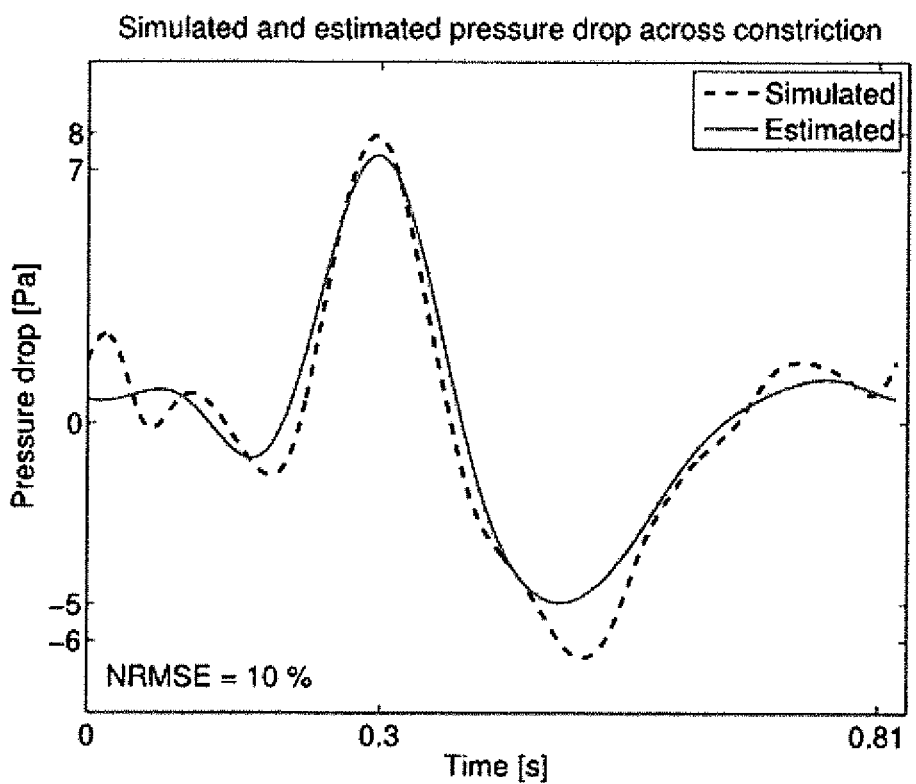
FIG. 8 shows the mean of three measured pressure profiles plotted together with a simulated pressure drop from an FE model.

The temporal evolution of the pressure drop for the three measured cardiac cycles is plotted in FIG. 7. The figure shows the greatest pressure drop in the systolic phase of the cardiac cycle, and that the drop peaks just before the flow reaches its maximum velocity. The average standard deviation across the pulse is found to 4% in reference to the maximum pressure of 7 Pa. The mean of the three measured pressure profiles is plotted together with the simulated pressure drop from the FE model in FIG. 8. A normalized root-mean-square error of 10% is found between the estimated data and the reference model.

In this example, non-invasive measurement of pressure changes has been calculated from vector velocity data. The intravascular pressure drop across the constricted phantom varied depending on when in the cardiac cycle it was measured. The largest drop was estimated just prior to the peak systolic phase, reaching 7 Pa with a standard deviation of 4%. A normalized error of 10% was seen between the estimated pressure and the results from the FE model. For this example, the approached described herein employs vector velocity data acquired to a depth of 3 cm using directional synthetic aperture flow imaging, producing 1,500 velocity frames a second.

Such techniques otherwise allow for averaging across estimates without compromising the peak of the profile. Averaging is beneficial as it essentially performs a low-pass filtering of the estimates, thus, avoiding the higher frequency content, which usually is associated with noise. Noise cancellation can be used for deriving proper derivatives, and can become important when moving into higher order derivatives. The effect of viscosity, which is related to second-order differentiation, gets introduced when studying flow in smaller vessel where the influence from the wall is more prominent. Therefore, pressure estimation by the Navier-Stokes equations should for those regions take the viscous forces into account.

The literature indicated a 24% overestimation of the peak systolic pressure from commonly employed catheters. The example herein showed results within 10% of the reference model and with a standard deviation of 4%, indicating that the approach described herein obtains pressure measurements that are more reliable than an invasive catheter. Superseding catheters in the clinic may eliminate the need for such invasive procedures and their appertaining X-ray radiation for guidance of the catheter.

Figure 9:
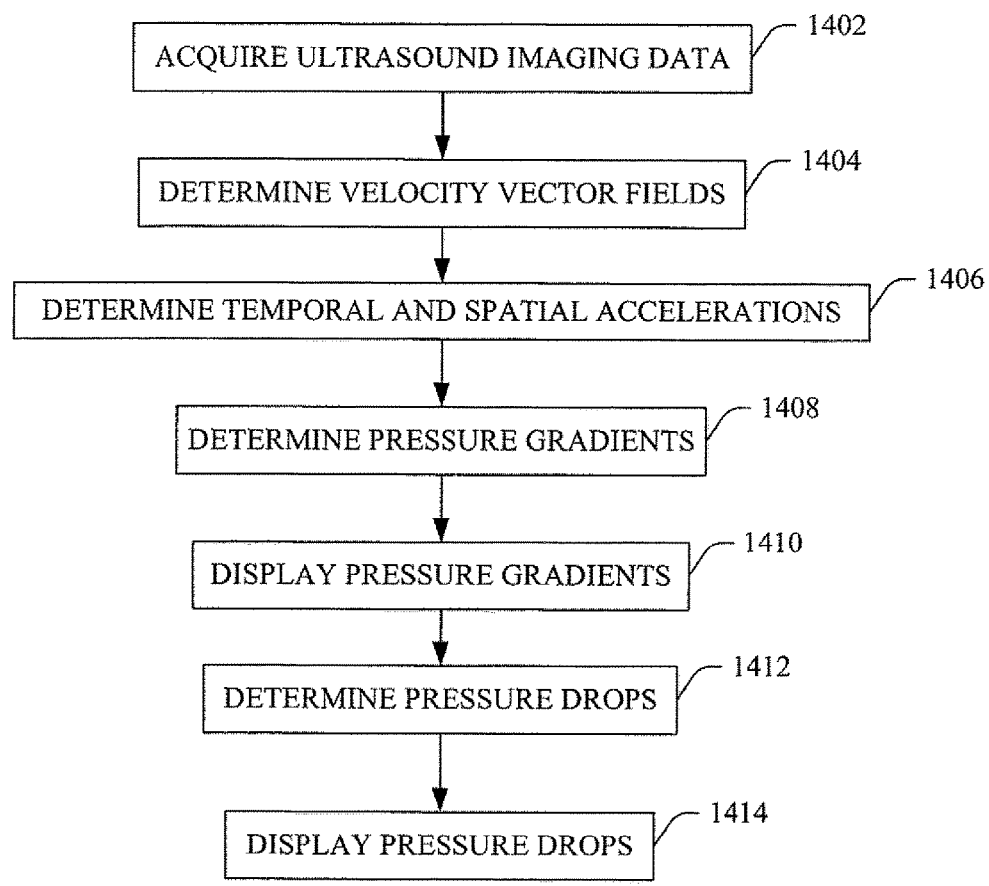
FIG. 9 illustrates a method.

FIG. 9 illustrates a method.

It is to be understood that the following acts are provided for explanatory purposes and are not limiting. As such, one or more of the acts may be omitted, one or more acts may be added, one or more acts may occur in a different order (including simultaneously with another act), etc.

At 1402, ultrasound imaging data is acquired. It is to be appreciated that ultrasound imaging data can be acquired in near real-time and thus provides higher timer resolution data for superior filter, e.g., relative to MR and/or other imaging modalities, where data is averaged data over time due to slower acquisition capabilities.

At 1404, vector velocity fields are determined from the acquired ultrasound imaging data. As described herein, this includes 2-D and/or 3-D velocity vector fields determined using various approaches such as a transverse oscillation, plane wave, synthetic aperture, etc.

At 1406, temporal and spatial acceleration components are determined based on the velocity vector fields, as described herein and/or otherwise.

At 1408, pressure gradients are estimated from the temporal and spatial acceleration components, as described herein and/or otherwise.

At 1410, the pressure gradients are presented, as described herein and/or otherwise.

At 1412, one or more pressure drops are determined based on the pressure gradients, as described herein and/or otherwise.

At 1414, the pressure drops are presented, as described herein and/or otherwise.

In another embodiment, acts 1410 and 1412 are omitted.

The pressure gradients and/or drops can be conveyed to another device. The other device can be a display, hardware memory, another device, etc. In one instance, a pressure gradient and/or drop that crosses a predetermined threshold level cause the other device to perform an act. For example, the drop may cause the other device to invoke an alarm, transmit a notification to a smartphone, page, or the like, sense another physiologic parameter, etc.

The methods described herein may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A method for determining pressure gradients with ultrasound data, the method comprising:
   acquiring ultrasound data of a vessel;
   generating a velocity vector profile for flow in the vessel with the ultrasound data;
   computing an acceleration with the velocity vector profile, wherein the acceleration includes at least a temporal acceleration, and computing the temporal acceleration includes:
      transforming the velocity vector profile from a time domain to a frequency domain;
      selecting a sub-set of the frequency components that satisfy predetermined energy criteria;
      processing the selected sub-set by differentiating the selected sub-set;
      transforming the differentiated selected sub-set back to the time domain, thereby reducing noise from the velocity vector profile and determining the temporal acceleration from the noise-reduced velocity data;
   determining the pressure gradients with the computed acceleration; and
   displaying an ultrasound image of the vessel with indicia indicative of the pressure gradients superimposed thereover.

2. The method of claim 1, wherein the pressure gradients are generated using the Navier-Stokes equation.

3. The method of claim 1, wherein the selecting of the sub-set of the frequency components further includes selecting based on a complexity of the velocity vector.

4. The method of claim 3, wherein the transforming of the differentiated selected sub-set back to the time domain includes employing a trigonometric function that reconstructs the data back into the time domain.

5. The method of claim 3, wherein transforming the velocity vector profile to the frequency domain includes applying a Fourier transform to the velocity vector profile.

6. The method of claim 3, wherein the selecting of the sub-set of the frequency components further includes selecting the sub-set of frequency components based on an ability to recover a predetermined percentage of the velocity profile from the sub-set.

7. The method of claim 3, wherein selecting the sub-set of the frequency components include selecting a sub-set of the frequency components based on a signal-to-noise ratio of the velocity vector profile.

8. The method of claim 3, wherein selecting the sub-set of the frequency components include selecting a sub-set of the frequency components with an energy ins a predetermined range.

9. The method of claim 1, wherein the acceleration further includes a spatial acceleration.

10. The method of claim 1, further comprising:
receiving an identification of a plurality of points of interest on the ultrasound image, wherein the plurality of points of interest are respectively located behind a constriction of the vessel, within the constriction, and before the constriction;
determining a pressure drop based on the pressure gradients for the plurality of points of interest;
visually identifying the plurality of points of interest on the displayed ultrasound image; and
displaying the determined pressure drop.

11. The method of claim 1, further comprising:
receiving a signal identifying a set of pixels in the image for a line along a long axis of the vessel;
determining a pressure drop by integrating over the pressure gradients corresponding to the identified set of pixels;
repeating the acts of receiving and determining for each image frame; and
visually presenting the pressure drops as a function of time.

12. The method of claim 11, further comprising:
repeating the acts of receiving, determining, repeating and presenting for a plurality of different lines along the long axis of the vessel each image frame to produce a plurality of pressure drops; and
visually presenting the plurality of pressure drops as a pressure map.

13. The method of claim 1, wherein the velocity vector profile is one of a 2-D or 3-D velocity vector profile.

14. The method of claim 1, further comprising:
generating the velocity vector profile based on at least one of a transverse oscillation, a plan wave, or a synthetic aperture algorithm.

15. An apparatus, comprising:
a velocity estimator that processes ultrasound image data acquired by an ultrasound imaging system and generates velocity vector fields based thereon;
a temporal acceleration processor that processes the velocity vector fields and generates a temporal acceleration, wherein the temporal acceleration processor filters the velocity vector fields while determining the temporal acceleration by:
decomposing the velocity vector fields into a series of sinusoids;
discarding a sub-set of the sinusoids that do not satisfy predetermined energy criteria;
differentiating the remaining sinusoids; and
reconstructing the differentiated data back to the time domain;
a spatial acceleration processor that processes the velocity vector fields and generates a spatial acceleration;
a pressure change estimator that estimates pressure gradients for the ultrasound data based on a model and the temporal and spatial accelerations; and
a display configured to display ultrasound image data and the pressure gradients estimates.

16. The apparatus of claim 15, wherein the model is based on the Navier-Stokes equation.

17. The apparatus of claim 15, wherein the remaining sinusoids include a set that recover the velocity vector fields to a predetermined percentage.

18. The apparatus of claim 15, wherein the spatial acceleration processor fits a second-order polynomial to a subset of adjacent data points by a linear least-squared approach and then calculates convolution coefficients from a least-squared model to approximate first-order derivatives to generate the spatial acceleration.

19. The apparatus of claim 15, further comprising:
determining one or more pressure drop based on the pressure gradients.

20. A non-transitory computer readable storage medium encoded with computer executable instructions which when executed by a processor of the computer causes the processor to:
acquire ultrasound data of a vessel;
determine a spatial acceleration based on velocity vector fields for the ultrasound data;
transform the velocity vector fields to the frequency domain, producing a sum of sinusoids;
differentiate a sub-set of the sinusoids satisfying a predetermined energy of interest, producing a sum of cosines;
reconstruct the sum of cosines to determine a temporal acceleration; and
determine a pressure change with the Navier-Stokes equation based on the spatial acceleration and the temporal acceleration; and
display an ultrasound image of the vessel with indicia indicative of the pressure change superimposed thereover.

* * * * *